United States Patent
Wang et al.

(10) Patent No.: US 12,265,085 B2
(45) Date of Patent: Apr. 1, 2025

(54) **METHOD FOR ANALYZING CONTENT AND DISTRIBUTION OF MICROPLASTICS IN MARINE *Cnidaria* ORGANISMS**

(71) Applicant: Zhejiang University, Zhejiang (CN)

(72) Inventors: Wei Wang, Zhejiang (CN); Jirong Hu, Zhejiang (CN); Qian Bao, Zhejiang (CN); Feiyang Ye, Zhejiang (CN); Qingfu Ye, Zhejiang (CN)

(73) Assignee: Zhejiang University, Hangzhou (CN)

( * ) Notice: Subject to any disclaimer, the term of this patent is extended or adjusted under 35 U.S.C. 154(b) by 0 days.

(21) Appl. No.: 18/735,079

(22) Filed: Jun. 5, 2024

(65) Prior Publication Data

US 2024/0319199 A1    Sep. 26, 2024

Related U.S. Application Data

(63) Continuation of application No. PCT/CN2023/103529, filed on Jun. 29, 2023.

(30) Foreign Application Priority Data

Dec. 20, 2022   (CN) .......................... 202211643061.0

(51) Int. Cl.
  *G01N 33/58* (2006.01)
  *G01N 1/42* (2006.01)
  *G01N 21/64* (2006.01)

(52) U.S. Cl.
  CPC ............. *G01N 33/582* (2013.01); *G01N 1/42* (2013.01); *G01N 21/6458* (2013.01); *G01N 2021/6439* (2013.01)

(58) Field of Classification Search
  CPC ... G01N 33/582; G01N 21/6458; G01N 21/64
  See application file for complete search history.

(56) References Cited

FOREIGN PATENT DOCUMENTS

| CN | 103411942 A | 11/2013 |
|---|---|---|
| CN | 115290615 A | 11/2022 |

OTHER PUBLICATIONS

Dong (2018, The Natural Ecology and Stock Enhancement of the Edible Jellyfish (*Rhopilema esculentum* Kishinouye, 1891) in the Liaodong Bay, Bohai Sea, China. InTech. doi: 10.5772/intechopen. 75576).*
Bamstedt (Marine Biology, 1999, 135: 89-98).*
Horn (Journal of Experimental Marine Biology and Ecology, vol. 481, Aug. 2016, pp. 41-48).*
Ding Environmental Pollution 238 (2018) 1-9.*
Zhang, Science of the Total Environment 648 (2019) 1431-1439.*
Widmer (Journal of the Marine Biological Association of the United Kingdom, 85 (3), 569-573).*
Sucharitakul. Marine Environmental Research 182 (2022) 105774 Available online Oct. 21, 2022.*
Microplastics ingestion in the ephyra stage of *Aurelia* sp. triggers acute and behavioral responses Elisa Costa etc., Ecotoxicology and Environmental Safety ; Nov. 27, 2019; p. 109983; Claims 1-7.
"Preliminary Study on Toxicological Effects of Polystyrene Nanoparticles on Mice", Fan Xingpei, "Dissertation for the Master Degree in Science"; pp. E055-58; Claims 1-7; Jan. 15, 2021.

\* cited by examiner

*Primary Examiner* — Valarie E Bertoglio

(57) ABSTRACT

Disclosed is a method for analyzing the content and distribution of microplastics in marine *Cnidaria* organisms, including: an exposure experiment of marine *Cnidaria* organisms; observation with a stereotype fluorescence microscope; plotting of a standard curve of fluorescence microplastics; sample fluorescence imaging and calculation of content of microplastics and freeze-drying of samples and calculation of a microplastics concentration. Technical solutions of the present disclosure can accurately position the distribution of microplastics in living marine *Cnidaria* organisms, and effectively and accurately quantify the content of microplastics in living organisms and local tissues, which is of great significance to the monitoring and treatment of new environmental pollutants.

1 Claim, 4 Drawing Sheets

METHOD FOR ANALYZING CONTENT AND DISTRIBUTION OF MICROPLASTICS IN MARINE *Cnidaria* ORGANISMS

CROSS-REFERENCE TO RELATED APPLICATIONS

This application is a continuation of PCT/CN2023/103529, filed Jun. 29, 2023 and claims priority of Chinese Patent Application No. 202211643061.0, filed on Dec. 20, 2022, the entire contents of which are incorporated herein by reference.

TECHNICAL FIELD

The present disclosure belongs to the field of environmental pollutant detection, and relates to a method for analyzing the content (enrichment) and distribution of microplastics in marine *Cnidaria* organisms, especially *Medusozoa* livings, which a method for positioning and quantitatively detecting microplastic particles based on a fluorescent tracer technique.

BACKGROUND

Due to the widespread use of plastic products, plastic products can be decomposed into microplastic particles with a diameter of less than 5 mm under the action of physical, chemical and biological factors. These microplastic particles widely exist in rivers, oceans and other water bodies. After being ingested by organisms, the microplastic particles show a variety of biological toxicity and pose a potential threat to aquatic organisms.

At present, the enrichment and distribution of microplastics in the aquatic organisms have some research progress, mainly focusing on the use of a microscope to count microplastic particles, to roughly determine the distribution of microplastics in different organs and tissues of organisms. However, since the microplastic particles are difficult to distinguish from other similar environmental particles in the field of view, the Fourier transform infrared spectrometer and Raman characterization are needed to characterize particles qualitatively, thus increasing the workload and complexity of microplastics localization and quantification in the organisms. In addition, the data obtained by a counting method have subjectivity and sampling error, so the content of microplastics cannot be accurately quantified. Moreover, other existing quantitative techniques require complex pretreatment processes (such as, the digestion of biological tissues) to extract microplastic particles in tissues, increasing the workload of detection. Therefore, it is of great environmental significance to develop a fluorescence-based living imaging method without complex pretreatment for studying the distribution and quantification of microplastics in vivo.

SUMMARY

In view of the limitations that pretreatment processes are complex in the prior art and it is unable to analyze the distribution and content of microplastics in aquatic organisms, the present disclosure provides a method for analyzing the content and distribution of microplastics in marine *Cnidaria* organisms, including the following steps.

An exposure experiment: fluorescent microplastics particles with specific diameters are added to artificial seawater to prepare an exposure solution system, and marine *Cnidaria* organisms are selected as subjects to carry out an exposure experiment.

Observation with a stereotype fluorescence microscope: the exposed subject livings or local tissues are transferred to a stereotype fluorescence microscope, and the distribution of microplastics in the whole subjects or the local tissues is observed using the stereotype fluorescence microscope.

Sample fluorescence imaging and calculation of content of microplastics: the exposed subject livings or the local tissues are placed in a detection chamber of a small animal living imager, fluorescence intensities in the subject livings or the local tissues are determined using the small animal living imager, and corresponding content is calculated according to a standard curve. The standard curve of fluorescent microplastics is plotted by the following method.

Solutions containing different contents of fluorescent microplastics are dropped into culture dishes and placed into the detection chamber of the small animal living imager, a fluorescence intensity of each of solutions is determined after specific excitation and emission wavelengths are set, and the standard curve of fluorescent microplastics is plotted according to the content of microplastics and the corresponding fluorescence intensity.

Further, the subject is a marine *Cnidaria* organism, which is *Medusozoa* or sea anemone, etc.

Further, a salinity of the artificial seawater in the exposure solution system is 20‰-30‰; a temperature of an exposure solution is 18-25° C.; and a diameter of microplastic is 100-1000 nm.

Further, the exposed subject livings or the local tissues are transferred under the stereotype fluorescence microscope and to the detection chamber of the small animal living imager using a culture dish as a container.

Preferably, a GFP-B typed light filter is used in the fluorescence microscope.

Further, the exposure experiment specifically includes that: the subject is placed into the exposure solution system for cultivation for a period of time, fished out, and cleaned with the artificial seawater for detection.

Further, the exposure experiment further includes that: a blank control group is set for deducting a background fluorescence value of the subject from the sample fluorescence imaging and the calculation of content of microplastic. Marine *Cnidaria* organisms in the blank control group are cultured in the artificial seawater.

Further, fluorescence imaging is performed on the subject livings using the small animal living imager.

Further, the method further includes that: the detected subject is freeze-dried, a dry weight of a sample is weighed, and the content of microplastics obtained by the sample fluorescence imaging is calculated to obtain the content of microplastics in unit mass of the tissue.

Further, a freeze-drying time is 48 h.

The present disclosure has the following advantages. The method of the present disclosure directly uses the stereotype fluorescence microscope and the small animal living imager to detect microplastics in the marine *Cnidaria* organisms, without processes such as the digestion of biological tissues, which can not only accurately position the distribution of microplastics in living marine *Cnidaria* organisms, but also greatly simplify the detection process, and effectively and accurately quantify the content of microplastics in the marine *Cnidaria* organisms. It is of great significance for the monitoring and treatment of new environmental pollutants and provides a method for studying the enrichment ability of microplastics in the marine *Cnidaria* organisms.

DETAILED DESCRIPTION

Figure 1:
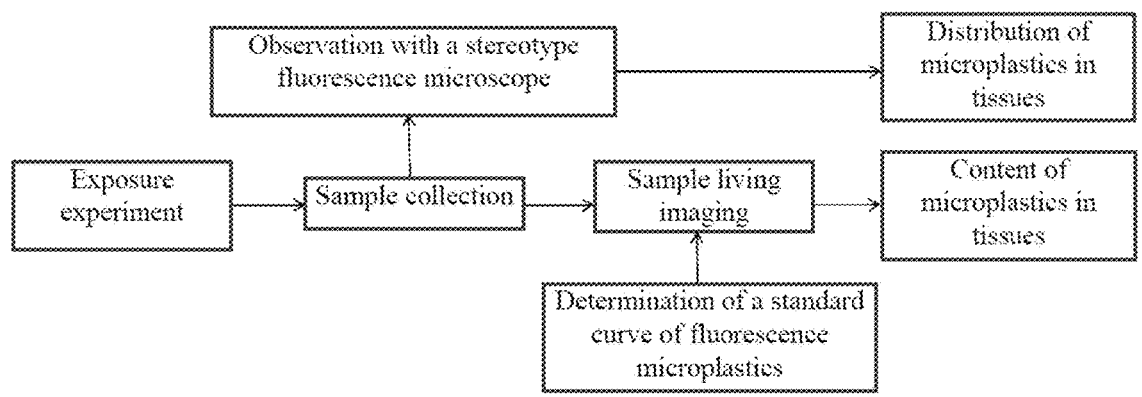
FIG. 1 shows a flow chart of a method of the present disclosure.

Disclosed in the present disclosure is a method for analyzing the content and distribution of microplastics in marine *Cnidaria* organisms, to lay a foundation for health risk assessment in microplastics. A flow of the method is shown in FIG. 1, including the following steps.

(1) An exposure experiment of marine *Cnidaria* organisms: fluorescent microplastics particles with specific diameters are added to artificial seawater to prepare an exposure solution system, and marine *Cnidaria* organisms are selected as subjects to carry out an exposure experiment.

(2) Observation with a stereotype fluorescence microscope: the exposed subjects are transferred to culture dishes, the culture dishes are placed under a stereotype fluorescence microscope, and the distribution of microplastics in the whole marine *Cnidaria* organisms is observed using the stereotype fluorescence microscope. The subjects can be divided into various tissue sites using a dissecting tool and observed sequentially, and a specific position of microplastics is positioned.

(3) Sample fluorescence imaging and calculation of content of microplastics: the exposed subjects are transferred to the culture dishes, the culture dishes are placed in a detection chamber of a small animal living imager, fluorescence intensities in the whole marine *Cnidaria* organisms are determined using the small animal living imager, and corresponding content is calculated according to a standard curve of fluorescence microplastics. Likewise, in this step, the marine *Cnidaria* organisms can also be divided into various tissue sites using the dissecting tool and transferred to culture dishes, the culture dishes are placed in the detection chamber of the small animal living imager, fluorescence intensities in various tissues are determined using the small animal living imager, and corresponding content of microplastics is calculated according to the standard curve of fluorescence microplastics.

The standard curve of fluorescence microplastics is plotted by the following methods. Solutions containing different contents of fluorescent microplastics are dropped into culture dishes, followed by placing into the detection chamber of the small animal living imager, a fluorescence intensity of each of solutions is determined after specific excitation and emission wavelengths are set (depending on the selected fluorescent marker), and the standard curve is plotted according to the content of microplastics and the corresponding fluorescence intensity.

(4) Freeze-drying of samples and calculation of a microplastics concentration: the detected samples are placed into a freeze-drier to dry, a dry weight of the samples is weighed, and the content of microplastics in step (3) is converted into the content of fluorescent microplastics in unit mass of the tissue.

In the above step, preferably, fluorescently labeled microplastic particles are used in step (1), with a diameter of 20-1000 nm.

In the above solution, preferably, subjects used in step (1) are *Medusozoans*, such as *Aurelia aurita* and *Rhopilema esculentum*.

Hereinafter, the present disclosure is described in detail by taking *Rhopilema esculentum* larvae as an example. The implementation examples are only used to further illustrate the present disclosure and do not represent the protection scope of the present disclosure. Non-essential modifications and adjustments made by others according to the present disclosure still belong to the protection scope of the present disclosure.

EXAMPLE

A method for analyzing the content and distribution of microplastics in marine *Cnidaria* organisms, as shown in FIG. 1, includes the following steps.

(1) An exposure experiment of *Medusozoans*: polystyrene microspheres (PS-MPs, with a diameter of 1 μm) labeled by a 4-chloro-7-nitro-1,2,3-benzoxadiazole (NBD-CL) fluorescent dye (with an excitation wavelength of 488 nm and an emission wavelength of 518 mm), as test substances, were added into artificial seawater to prepare an exposure solution. Healthy *Medusozoa* larvae with umbrella diameters of 2.5±0.5 cm were taken as test animals, followed by randomly dividing into an exposure group and a control group. In the exposure group, 3 PS-MPs had concentration levels of 0.1, 1 and 10 mg L−1 with an exposure period of 5 d. Other experimental conditions included a temperature of 22±1° C., a salinity of 25±1‰, a light cycle of alternating 12 h of light and 12 h of darkness, and feeding with brine shrimp nauplii every day. Living *Medusozoans* in the exposure group were placed into a container containing the exposure solution; and living *Medusozoans* in the control group were placed into the artificial seawater for cultivation for a period of time, *Medusozoans* were fished out of a glass bottle with a stainless medicine spoon, microplastics on surfaces of *Medusozoans* were washed with clean seawater, followed by transferring to the clean seawater, and the above steps were repeated for three times.

Figure 2:
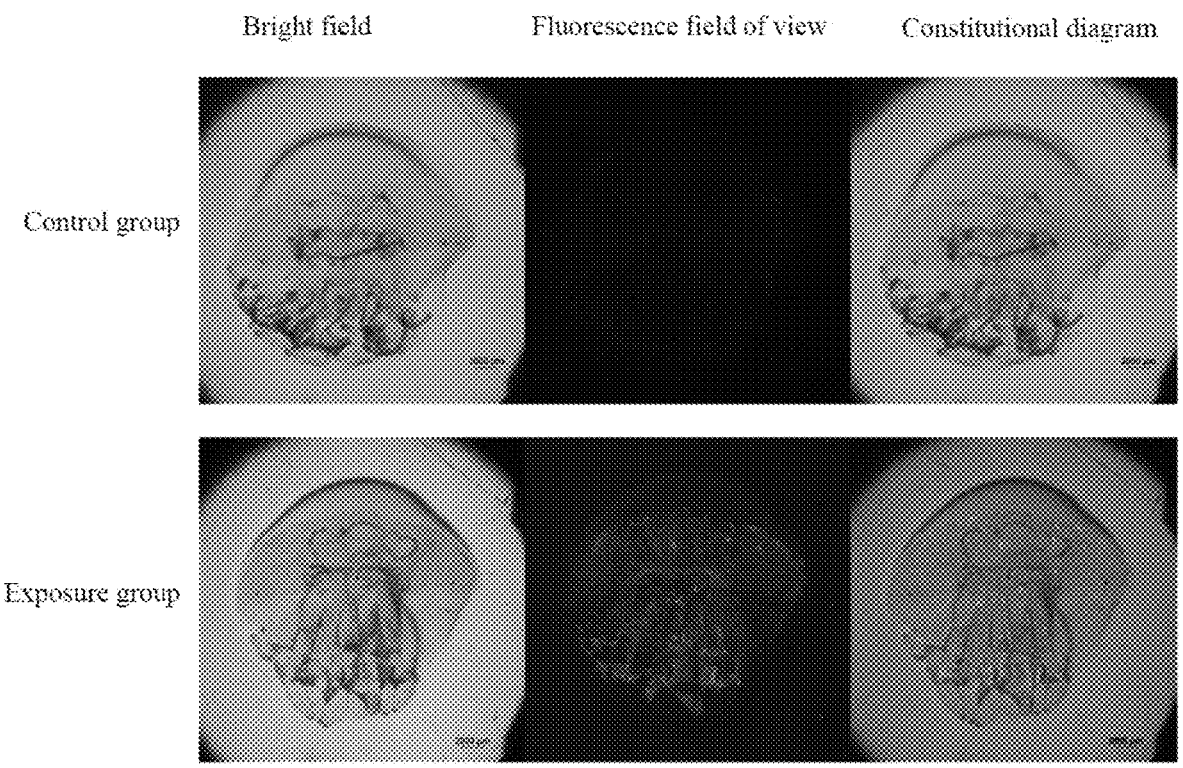
FIG. 2 shows the distribution of fluorescent microplastics in whole *Medusozoans*.
Figure 3:
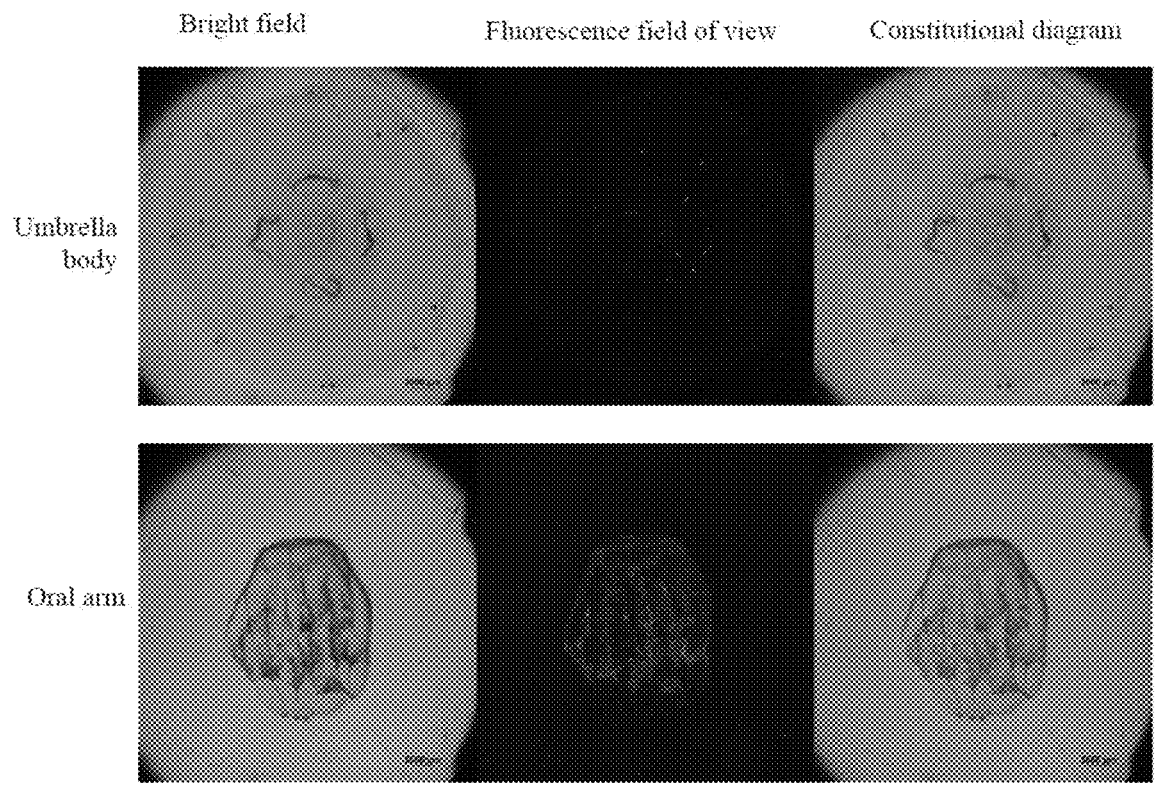
FIG. 3 shows the distribution of fluorescent microplastics in oral arms and umbrella bodies of *Medusozoans*.

(2) Observation with a stereotype fluorescence microscope: the distribution of microplastics in the whole living *Medusozoans* was positioned using a stereotype fluorescence microscope (Nikon SMZ18, Japan) after the exposure of *Medusozoans* to fluorescent microplastics for 5 d (at an exposure concentration of 10 mg L−1). A GFP-B typed light filter is used in the stereotype fluorescence microscope (with parameters: excitation filter (EX) 480/40, dichroic mirror (DM) 505, and bandwidth allocation (BA) 535/50). As shown in FIG. 2, the distribution of fluorescent microplastics in the whole *Medusozoa* livings can be clearly observed, and the distribution of microplastics enrichment in different tissue sites is different. In order to better determine the tissue distribution of microplastics in *Medusozoans*, each of *Medusozoans* was divided into an umbrella body and an oral arm using a dissecting tool, followed by observing with the stereotype fluorescence microscope The results are shown in FIG. 3.

Figure 4:
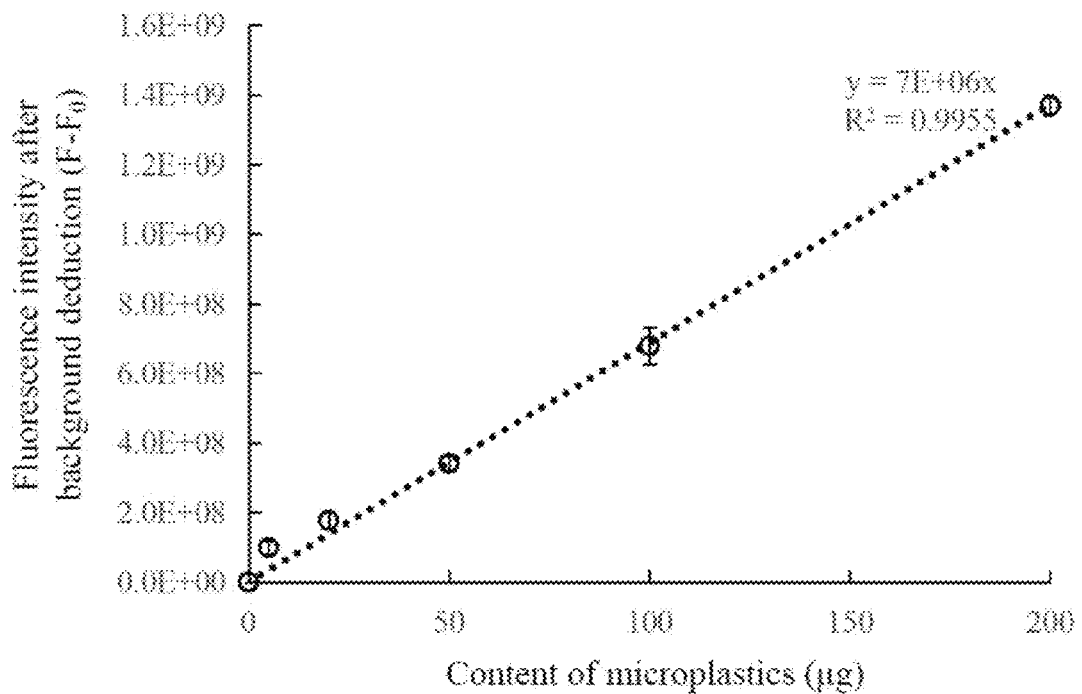
FIG. 4 shows a standard curve diagram of a fluorescence intensity of fluorescent microplastics varying with content.

(3) Plotting of a standard curve of fluorescence microplastics: gradient fluorescence microplastics solutions with different contents of microplastics were prepared, 1 mL of a standard solution was taken and dropped into a culture dish, the culture dish was placed into a detection chamber of a small animal living imaging system (in vivo imaging system (IVIS) Spectrum, USA), a fluorescence intensity of each of solutions was determined after specific excitation and emission wavelengths are set, and a standard curve of a fluorescence intensity varying with content of microplastics was plotted. In the example, the standard curve of fluorescence microplastics is set with the content of microplastics of 0, 5, 20, 50, 100 and 200 μg, and the standard curve is shown in FIG. 4.

Figure 5:
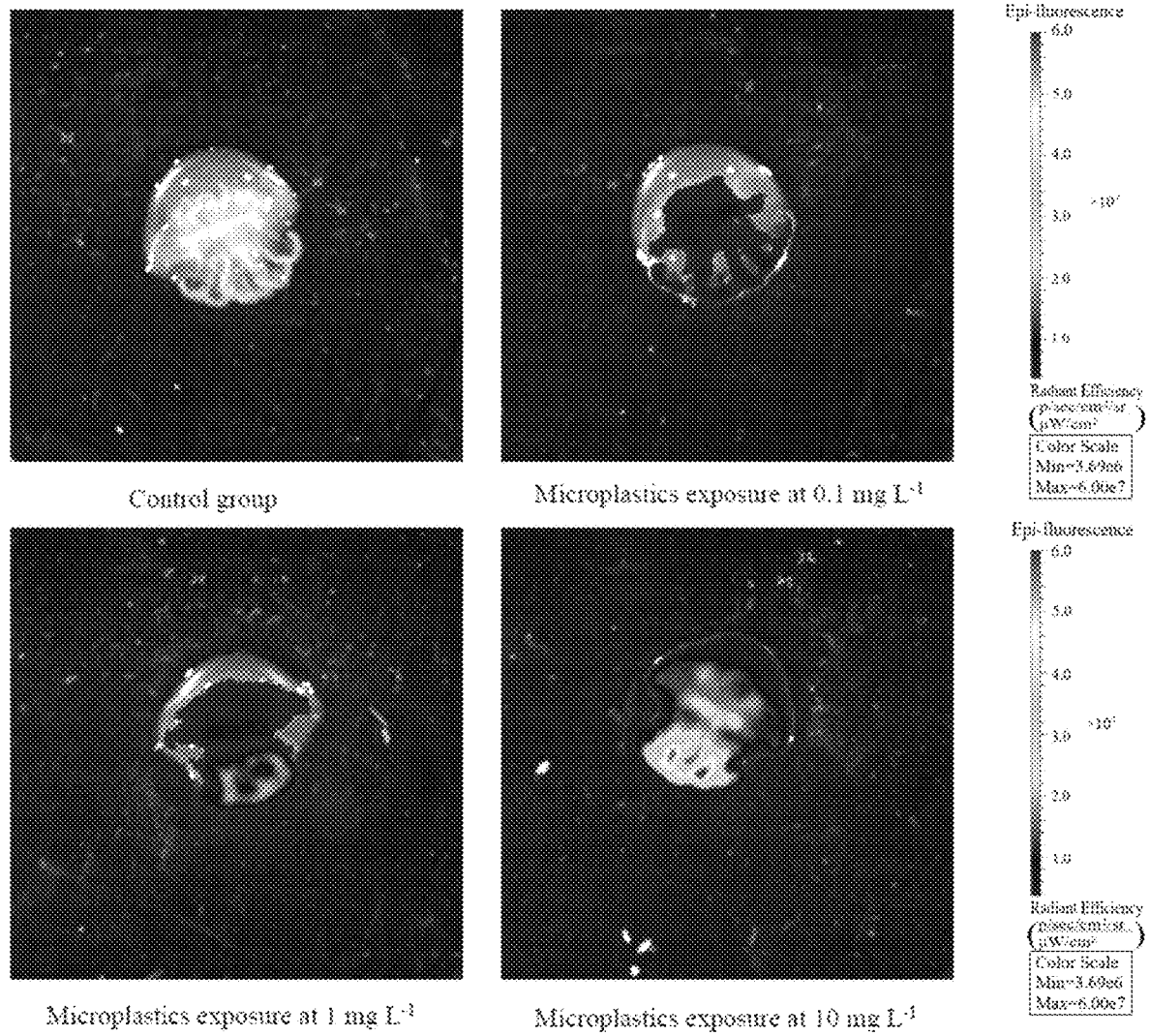
FIG. 5 shows fluorescence living imaging diagrams of *Medusozoans* exposed to seawater at different concentrations of fluorescent microplastics.

(4) Sample fluorescence imaging and calculation of content of microplastics: the living *Medusozoans* were transferred to the culture dish, fluorescence intensities in *Medusozoa* tissues were determined using the small animal living imager at the excitation and emission wavelengths of step (3), and corresponding content was calculated according to the standard curve. A background value of the blank control group was deducted from results of samples in the exposure group to obtain a final result. FIG. 5 shows fluorescence living imaging diagrams of *Medusozoans* exposed to seawater at different concentrations of fluorescent microplastics.

Figure 6:
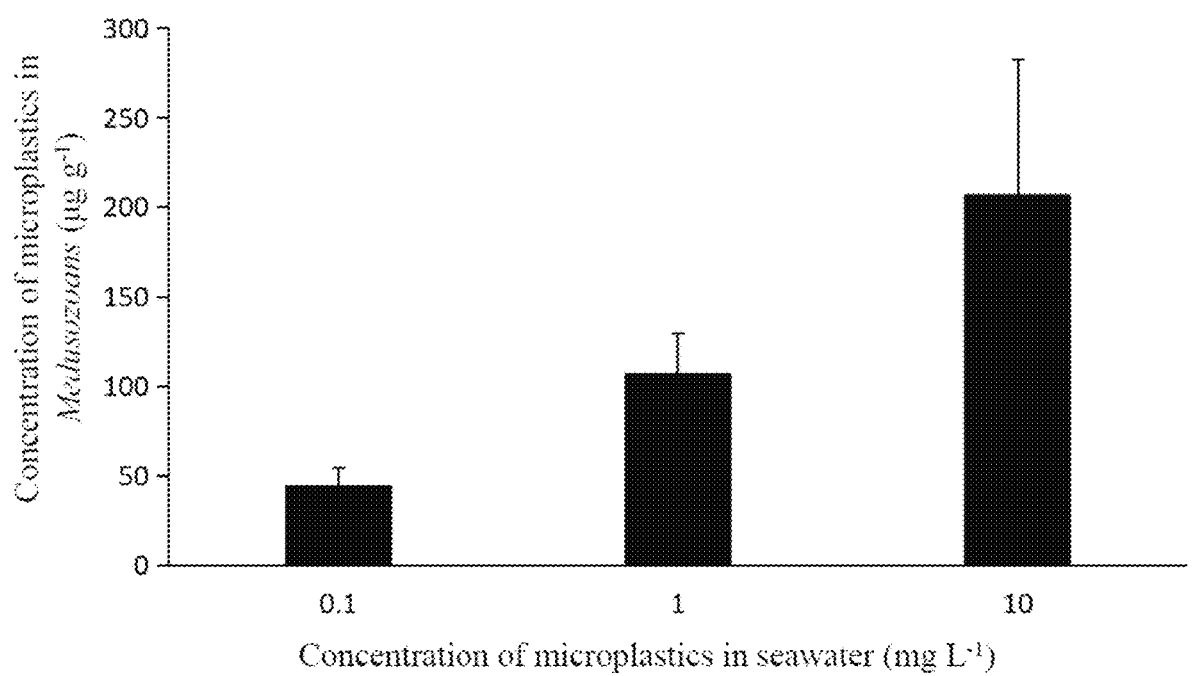
FIG. 6 shows the content of fluorescent microplastics in *Medusozoans*.

(5) Freeze-drying of samples and calculation of a microplastics concentration: the detected samples were placed into a freeze-drier to dry for 48 h, followed by weighing to obtain a dry weight of the *Medusozoa* tissues, and the content of microplastics in step (4) was converted into the content of fluorescent microplastics in unit mass of the tissue, as shown in FIG. 6.

The method of the present disclosure directly uses the stereotype fluorescence microscope and the small animal living imager to detect microplastics in marine *Cnidaria* organisms, without processes such as the digestion of biological tissues, which can not only accurately position the distribution of microplastics in living marine *Cnidaria* organisms, but also greatly simplify the detection process, and effectively and accurately quantify the content of microplastics in the marine *Cnidaria* organisms. It is of great significance for the monitoring and treatment of new environmental pollutants.

The invention claimed is:

1. A method for analyzing the content and distribution of microplastics in *Medusozoans*, comprising the steps of:
   (1) an exposure experiment of *Medusozoans*: adding polystyrene microspheres (PS-MPs) with a diameter of 1 μm labeled by a 4-chloro-7-nitro-1,2,3-benzoxadiazole (NBD-CL) fluorescent dye with an excitation wavelength of 488 nm and an emission wavelength of 518 mm, as test substances, into artificial seawater to prepare an exposure solution;

taking healthy juvenile jellyfish with umbrella diameters of 2.5±0.5 cm as test animals, followed by randomly dividing into an exposure group and a control group, in the exposure group, 3 PS-MPs having concentration levels of 0.1 mg $L^{-1}$, 1 mg $L^{-1}$ and 10 mg $L^{-1}$ with an exposure period of 5 d, and other experimental conditions comprising a temperature of 22±1° C., a salinity of 25±1% ‰, a light cycle of alternating 12 h of light and 12 h of darkness, and feeding with brine shrimp nauplii every day; and placing living *Medusozoans* in the exposure group into a container containing the exposure solution; and placing living *Medusozoans* in the control group into the artificial seawater for cultivation for a period of time, fishing *Medusozoans* out of a glass bottle with a stainless medicine spoon, washing microplastics on surfaces of *Medusozoans* with clean seawater, followed by transferring to the clean seawater, and repeating the above steps for three times;

(2) observation with a stereotype fluorescence microscope: positioning the distribution of microplastics in the whole living *Medusozoans* using a stereotype fluorescence microscope after the exposure of *Medusozoans* to fluorescent microplastics at an exposure concentration of 10 mg $L^{-1}$ for 5 d, a GFP-B typed light filter being used in the stereotype fluorescence microscope;

(3) plotting of a standard curve of fluorescence microplastics: preparing gradient fluorescence microplastics solutions with different contents of microplastics, taking 1 mL of a standard solution and dropping the same into a culture dish, placing the culture dish into a detection chamber of a small animal living imager, determining fluorescence intensities of each of solutions after specific excitation and emission wavelengths are set, and plotting a standard curve of a fluorescence intensity varying with content of microplastics, wherein the standard curve of fluorescence microplastics is set with the contents of microplastics of 0 μg, 5 μg, 20 μg, 50 μg, 100 μg and 200 μg;

(4) sample fluorescence imaging and calculation of content of microplastics: transferring the living *Medusozoans* to the culture dish, determining fluorescence intensities in *Medusozoa* tissues using the small animal living imager at the excitation and emission wavelengths of step (3), and calculating corresponding content according to the standard curve, a background value of the blank control group being deducted from results of samples in the exposure group to obtain a final result; and (5) freeze-drying of samples and calculation of a microplastics concentration: placing the tested samples into a freeze-drier to dry for 48 h, followed by weighing to obtain a dry weight of the *Medusozoa* tissues, and converting the content of microplastics in step (4) into the content of fluorescent microplastics in unit mass of the tissue.

* * * * *